United States Patent [19]

Tanaka et al.

[11] Patent Number: 5,385,393
[45] Date of Patent: Jan. 31, 1995

[54] DEVICE FOR CALCULATING COEFFICIENT OF FRICTION OF ROAD SURFACE

[75] Inventors: Keishin Tanaka; Toichiro Hikichi; Chiaki Kumagai, all of Wako, Japan

[73] Assignee: Honda Giken Kogyo Kabushiki Kaisha, Tokyo, Japan

[21] Appl. No.: 77,628

[22] Filed: Jun. 17, 1993

[30] Foreign Application Priority Data

Jun. 24, 1992 [JP] Japan ................. 4-166242

[51] Int. Cl.$^6$ ............................................. B60T 8/70
[52] U.S. Cl. ..................... 303/106; 303/103; 303/111
[58] Field of Search ............ 303/111, 103, 102, 106, 303/107, 108, 105, 110, 100, 109, 104, 97; 188/181 C, 181 A; 364/426.01, 426.02, 426.03; 180/197

[56] References Cited

U.S. PATENT DOCUMENTS

| | | | |
|---|---|---|---|
| 4,947,332 | 8/1990 | Ghoneim | 303/97 |
| 5,092,662 | 3/1992 | Okubo | 303/103 |
| 5,123,715 | 6/1992 | Okubo | 303/103 |
| 5,185,702 | 2/1993 | Okubo | 303/103 |
| 5,211,452 | 5/1993 | Okazaki et al. | 303/104 |
| 5,216,608 | 6/1993 | Ito et al. | 180/197 |
| 5,236,255 | 8/1993 | Kuwana et al. | 303/106 |
| 5,244,259 | 9/1993 | Pickenhahn et al. | 303/111 |
| 5,249,641 | 10/1993 | Sakata | 303/103 |
| 5,249,848 | 10/1993 | Matsuto et al. | 303/105 |
| 5,249,851 | 10/1993 | Johnsen | 303/104 |
| 5,255,193 | 10/1993 | Katayose et al. | 303/106 |
| 5,286,097 | 2/1994 | Myoi et al. | 303/109 |

FOREIGN PATENT DOCUMENTS

| | | |
|---|---|---|
| 0442500 | 8/1991 | European Pat. Off. . |
| 0533436 | 3/1993 | European Pat. Off. . |
| 62-194963 | 8/1987 | Japan . |
| WO91/09759 | 7/1991 | WIPO . |

*Primary Examiner*—Douglas C. Butler

[57] ABSTRACT

A device for controlling the braking force of a motorcycle in two controlling modes: a normal mode and an antilocking mode, comprises tachometers mounted on front and rear wheels of the motorcycle, an accelerometer mounted on the motorcycle body, and a control circuit. The control circuit calculates a peripheral acceleration of each wheel based on the peripheral velocity of each wheel, and a slippage ratio of each wheel based on the peripheral velocity of the wheel and the acceleration of the motorcycle body. When the slippage ratio and the peripheral acceleration of one wheel meets given conditions, the control circuit starts, prior to entering into the antilocking mode from the normal mode, to calculate the coefficient of friction between the road surface and the one wheel. For the other wheel, the coefficient of friction is calculated in the same manner.

3 Claims, 6 Drawing Sheets

DEVICE FOR CALCULATING COEFFICIENT OF FRICTION OF ROAD SURFACE

BACKGROUND OF THE INVENTION

1. Field of the Invention

This invention relates to a device for calculating the coefficient of friction between a wheel and a road surface, for use in a brake control system or a drive power control apparatus for motor vehicles.

2. Description of Background Art

A brake control system has been known for motor vehicles such as motorcars or motorcycles, which calculates a slippage ratio for each wheel with respect to a road surface based on the running speed of the vehicle and the peripheral speed of each wheel, and applies the optimum braking force to the vehicle based on the calculated slippage ratios.

In the conventional brake control system, the hydraulic pressure of a brake is increased proportionally to the amount of depression of a brake pedal until a predetermined slippage ratio (hereinafter called a "target slippage ratio"), at which braking force becomes the maximum, is reached (hereinafter called "normal control mode"). After the target slippage ratio has been attained, the control mode is shifted to limiting increase in the hydraulic pressure of the brake so as to avoid a further increase in the slippage ratio (hereinafter called a "limiting control mode" or an "antilock control mode").

There is a relationship between a slippage ratio of each wheel with respect to the road surface and the coefficient of friction $\mu$ of the road surface, namely, the slippage ratio, at which a vehicle can stably be controlled, which differs between road surfaces to one having a high coefficient of friction (hereinafter called a "high $\mu$ road") and the other having a low coefficient of friction (hereinafter called a "low $\mu$ road").

A high $\mu$ road is usually assumed, in the conventional brake control system, in setting a target slippage ratio, and upon entering into the limiting control mode, the coefficient of friction $\mu$ between the wheel and an actual road surface is then calculated to change over the target slippage ratio to another, thereby to enlarge the range in which the normal control mode is applicable. There has been disclosed in Japanese Patent Application Laid-Open Publication No. 62-194963 such a technical idea of detecting the coefficient of friction $\mu$ between the wheel and the actual road surface at the time of shifting the control modes from normal to limiting.

However, in the conventional brake control system described above, there was the danger of setting a suitable target slippage ratio too late, namely, after the control mode shift.

SUMMARY OF THE INVENTION

The present invention was made to solve the above problem. Therefore, the object of the present invention is to provide a device for calculating the coefficient of friction between a desired wheel and a road surface to determine a target slippage ratio at a suitable time.

To achieve the above object, the device according to the present invention, for a vehicle having a front wheel and a rear wheel, comprises first slippage ratio calculating means for calculating a slippage ratio of one of the front and rear wheels from a peripheral speed of the one wheel and the velocity of the vehicle, second slippage ratio calculating means for calculating a slippage ratio of the other wheel from a peripheral speed of the other wheel and the velocity of the vehicle, vehicle acceleration detecting means for detecting acceleration or deceleration of the vehicle, wheel acceleration calculating means for calculating peripheral acceleration or deceleration of the one wheel based on the peripheral speed of the one wheel, instructing means for generating a calculation starting signal when the slippage ratio of the one wheel and the peripheral acceleration of said one wheel respectively satisfy predetermined conditions, and friction coefficient calculating means for calculating the coefficient of friction between of the road surface and the one wheel based on the slippage ratio of the other wheel and the acceleration of the vehicle in response to the calculation starting signal.

According to the device of the present invention, the calculation starting signal is outputted by the instructing means only when both the slippage ratio of one of the front and rear wheels, which has been determined by the first slippage ratio calculating means, and the peripheral acceleration or deceleration of the one wheel which has been determined by the wheel acceleration calculating means, respectively, satisfy the predetermined conditions. Then, the friction coefficient calculating means calculates the coefficient of friction between the one wheel and the road surface based on the acceleration of the vehicle and the slippage ratio of the other wheel in response to the above signal. Thus, if the predetermined conditions have been suitably set, then the vehicle can be stably driven when it is braked, because the vehicle is controlled based on the coefficient of friction which has already been obtained.

Preferably, the instructing means produces the calculation starting signal when the peripheral deceleration of one wheel reaches a predetermined value or greater and the slippage ratio of the one wheel becomes positive.

More preferably, the friction coefficient calculating means determines a coefficient of friction between the road surface and the one wheel using the following equation:

$$\mu = (A - B \cdot K_x) \cdot G_x,$$

where $\mu$ represents the coefficient of friction between a road surface and one wheel; A and B are constants; $K_x$ is a constant set according to the slippage ratio of the other wheel in order to determine the coefficient of friction $\mu$ between the road surface and the one wheel regardless of the braking force of the other wheel; and $G_x$ is the acceleration of the vehicle.

The above and other objects, features and advantages of the present invention will become apparent from the following description and the appended claims, taken in conjunction with the accompanying drawings in which preferred embodiments of the present invention are shown by way of illustrative example.

DETAILED DESCRIPTION OF THE PREFERRED EMBODIMENTS

A device 30 for calculating the coefficient of friction of a road surface, according to the present invention, will be described in detail with reference to the accompanying drawings in which a preferred embodiment is shown by way of illustrative example.

Figure 2:
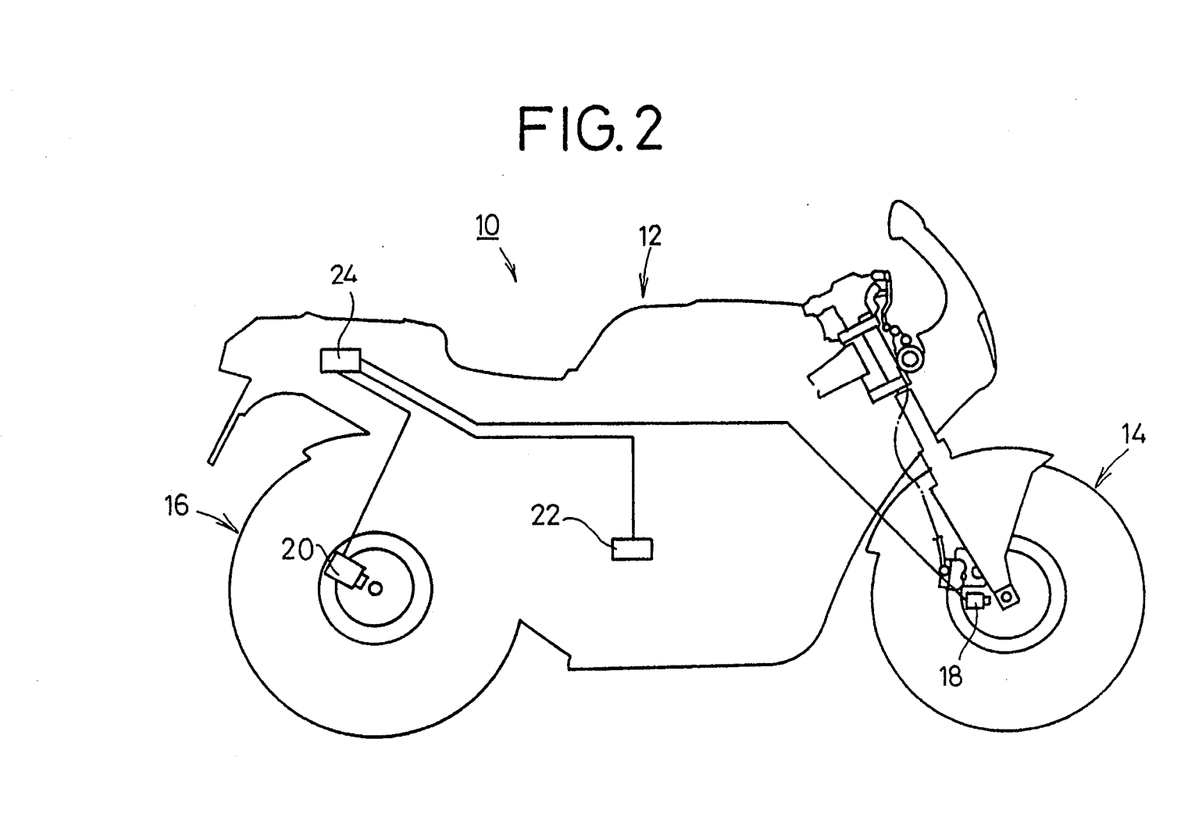
FIG. 2 is a view for describing a motorcycle in which the device shown in FIG. 1 is equipped.

In FIG. 2, a motorcycle 10 comprises a main body 12, a front wheel (driven wheel) 14 and a rear wheel (driving wheel) 16. Tachometers 18 and 20, each comprising a rotary encoder or the like, are respectively mounted on the front and rear wheels 14 and 16. A body accelerometer 22 is attached to the main body 12. These sensors 18, 20 and 22 are electrically connected to a control unit 24. The device 30 for calculating the coefficient of friction of the road surface is made up of these components.

Figure 1:
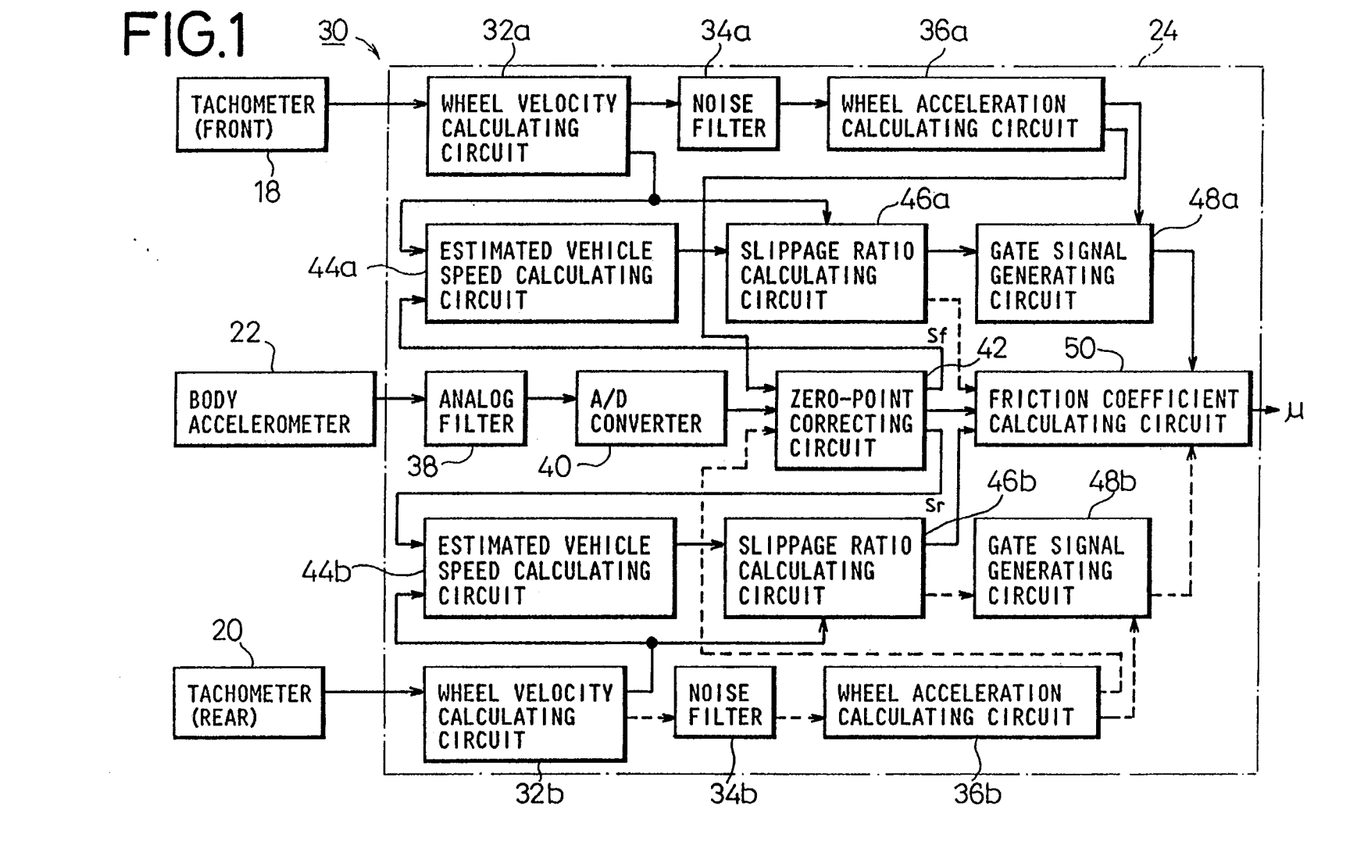
FIG. 1 is a block diagram showing the overall structure of a device for calculating the coefficient of friction of a road surface, according to the present invention.

The control unit 24 comprises wheel speed calculating circuits 32a and 32b for respectively calculating the peripheral speed $V_{wf}$ and $V_{wr}$ of the front and rear wheels 14 and 16, based on the output of respective tachometers 18 and 20, noise filters 34a and 34b for removing noise from the outputs of the wheel speed calculating circuits 32a and 32b, respectively, wheel acceleration calculating circuits 36a and 36b for respectively computing the peripheral acceleration $a_{wf}$ and $a_{wr}$ of the front and rear wheels 14 and 16, based on the respective noise-removed peripheral speed $V_{wf}$ and $V_{wr}$ of the wheels, an analog filter 38 for eliminating noise from a signal outputted from the body accelerometer 22, an A/D converter 40 for converting the noise-free output of the analog filter 38 into a digital signal, a zero-point correcting circuit 42 for correcting the output of the body accelerometer 22 passed through the A/D converter 40 to remove effects of pitch of the vehicle or the like, vehicle velocity estimating circuits 44a and 44b for respectively computing estimated velocities of the vehicle $V_{reff}$ and $V_{refr}$ based on the peripheral speed $V_{wf}$ and $V_{wr}$ of the wheels and the zero-point corrected acceleration of the vehicle $G_x$, slippage ratio calculating circuits 46a and 46b for respectively calculating slippage ratios $S_f$ and $S_r$ of the front and rear wheels 14 and 16, based on the respective estimated velocities of the vehicle $V_{reff}$ and $V_{refw}$ and the respective peripheral speed of the wheels $V_{wf}$ or $V_{wr}$, gate signal generating circuits 48a and 48b for respectively generating gate signals based on the respective peripheral acceleration of the wheels $a_{wf}$ and $a_{wr}$ and the respective slippage ratios $S_f$ and $S_r$, and a friction coefficient calculating circuit 50 for respectively calculating the coefficients of friction $\mu_f$ and $\mu_r$ between the road surface and the respective wheels, based on the zero-point corrected acceleration of the vehicle $G_x$ and the slippage ratio of the other wheel $S_r$ or $S_f$, in response to the respective gate signals generated by the gate signal generating circuits 48a and 48b.

Now, the operation in the device 30 constructed as described above will be described.

Figure 3:
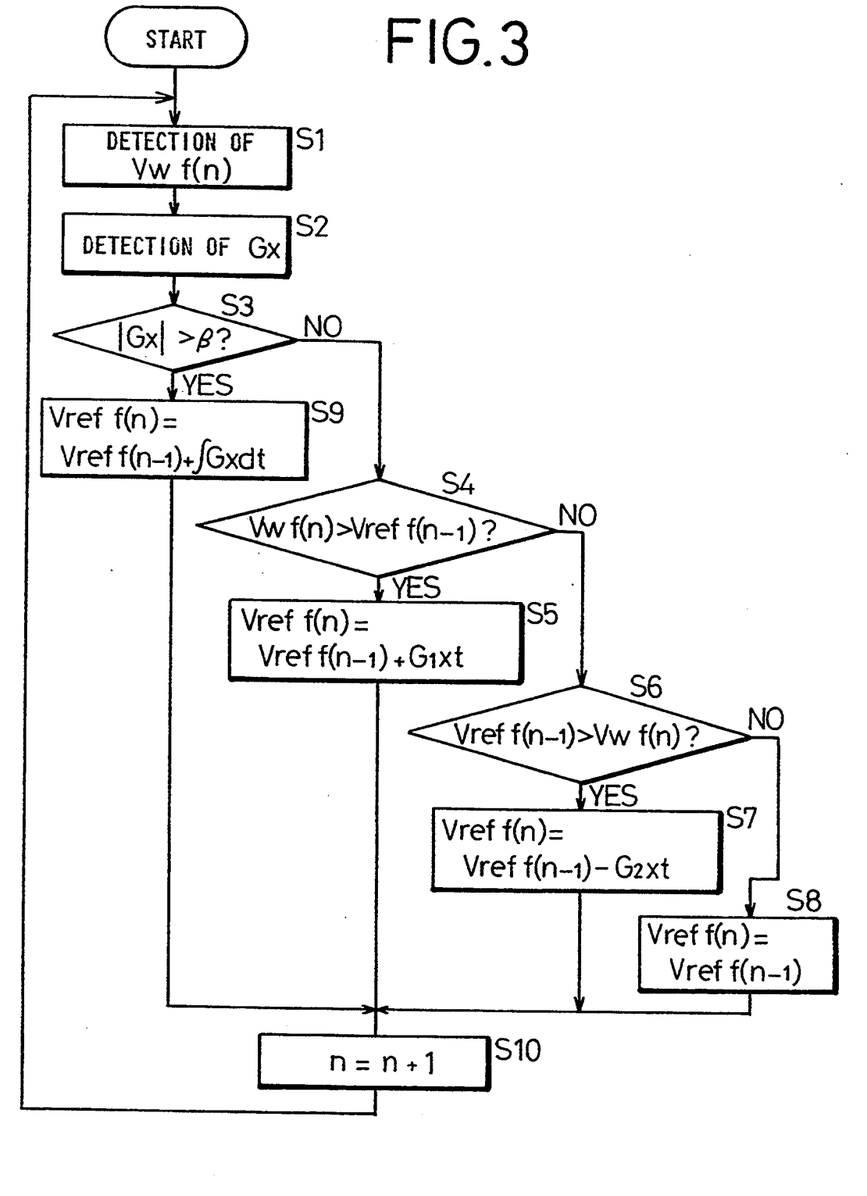
FIG. 3 is a flowchart for describing the way of calculating an estimated velocity of the vehicle by the device shown in FIG. 1.

First, a description regarding determination of the estimated velocity of the vehicle will be made with reference to a process flow chart of FIG. 3, and diagrams of FIGS. 4 and 5. There are two estimated velocities of the vehicle, $V_{reff}$ and $V_{refr}$, calculated based on the peripheral speed of the driven (front) and driving (rear) wheels 14 and 16, respectively. Hereinafter, determination of the estimated velocity of the vehicle $V_{reff}$ (based on the front wheel), for example, is described.

Figure 4:
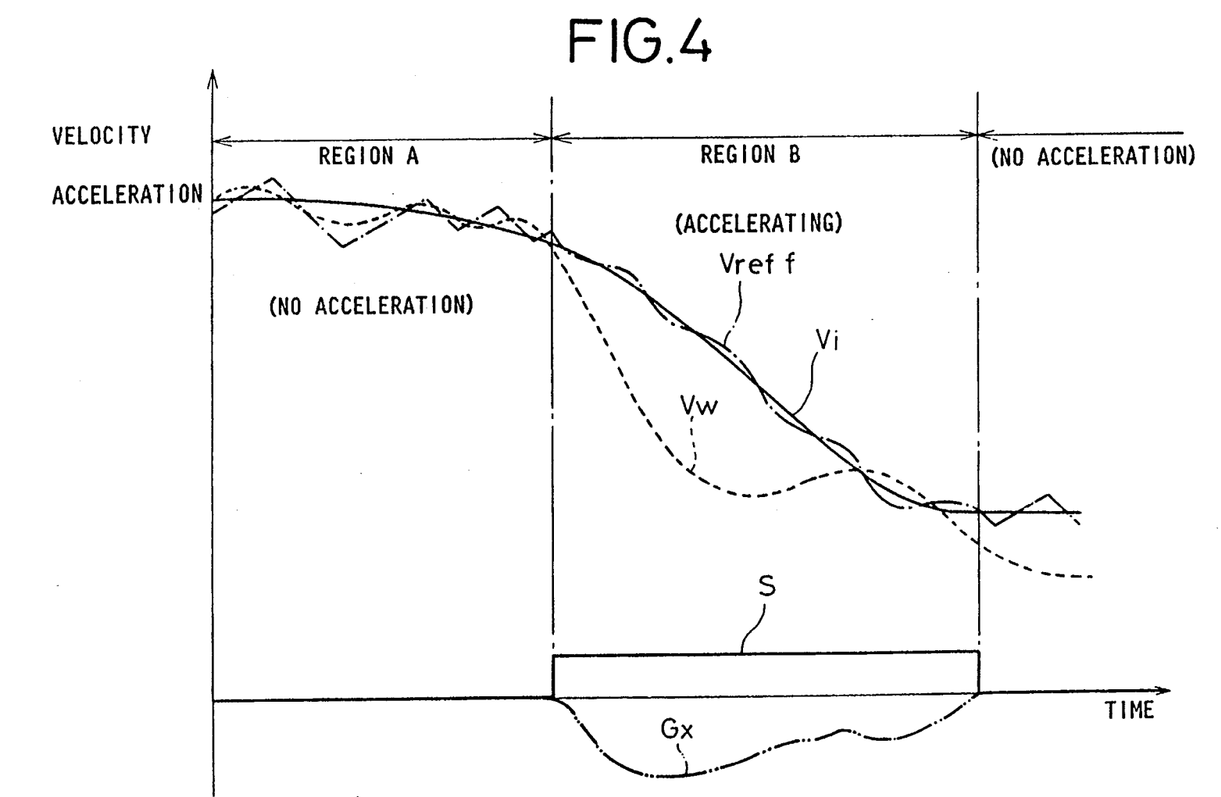
FIG. 4 is a graph for explaining the relationship between variables in estimating the velocity of the vehicle by the device shown in FIG. 1.
Figure 5:
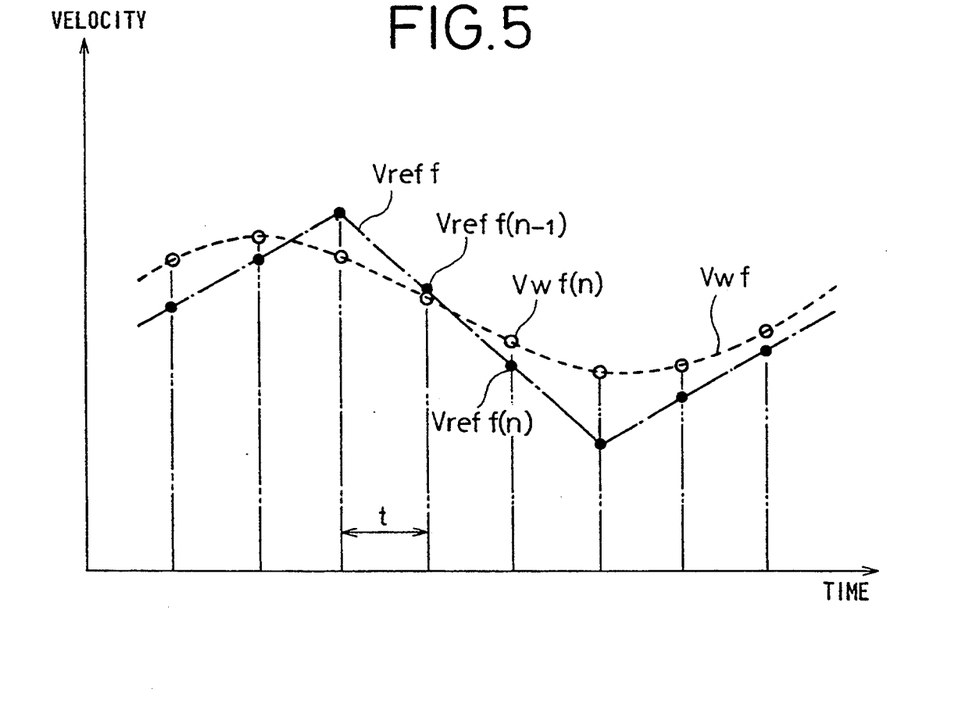
FIG. 5 is a graph for explaining the way of estimating the velocity of the vehicle by the device shown in FIG. 1.

In FIG. 4, there is shown a relationship between an actual velocity of the vehicle $V_i$ (solid line), the peripheral velocity of the wheel $V_{wf}$ (dashed line) and the estimated velocity of the vehicle $V_{reff}$ (chain line). The peripheral velocity of the wheel $V_{fw}$ and the estimated velocity of the vehicle $V_{reff}$ are determined by the device 30. The actual velocity of the vehicle $V_i$ is shown for demonstrating the reliability of the estimated velocity of the vehicle $V_{reff}$, which has been experimentally measured by a high-precision laser Doppler radar, a velocity detecting wheel or the like. These experimental devices cannot be equipped on actual vehicles because of their cost, size or weight. But the friction coefficients of the road can be obtained with sufficient accuracy by the device according to the invention without these expensive devices. The graph of FIG. 4 is divided into two regions, a region A in which the vehicle is not substantially being accelerated, and a region B in which an amount of acceleration (or deceleration) is occurring. FIG. 5 is a diagram showing the region A of FIG. 4 on a larger scale (actual velocity $V_i$ is not shown).

In the device 30, whether the vehicle is being accelerated (or decelerated) is determined based on the acceleration of the vehicle $G_{x'}$ and separate methods of calculating the estimated velocity of the vehicle $V_{reff}$ are employed depending in which region the acceleration of the vehicle $G_x$ falls: in the region A or the region B of FIG. 4. The vehicle velocity estimating circuit 44a, calculates the estimated velocity of the vehicle $V_{reff(n)}$ for each predetermined computing interval t in the following manner. Here, (n) in $V_{reff(n)}$ means that it is a value obtained in an nth computing cycle.

During a time period in which the motorcycle 10 is running, the tachometer 18 first detects the rotational speed of the driven wheel (front wheel 14) as a pulse train and outputs it to the wheel velocity calculating circuit 32a. The wheel velocity calculating circuit 32a calculates the peripheral velocity of the front wheel $V_{wf(n)}$ based on the pulse count in a predetermined time period (Step S1) and outputs it to the estimated vehicle velocity calculating circuit 44a and to the wheel acceleration calculating circuit 36a via the noise filter 34a. The wheel acceleration calculating circuit 36a differentiates the peripheral velocity of the wheel $V_{wf}$ to determine a peripheral acceleration $a_{wf}$ of the wheel.

The output signal of the body accelerometer 22 is inputted to the zero-point correcting circuit 42 via the analog filter 38 and the A/D converter 40. The zero-point correcting circuit 42 corrects the zero-point shift in the output signal of the body accelerometer 22, and removes a gravity component toward the vehicle travelling direction, due to a pitch motion of the vehicle body caused by up hill or down hill, from the output signal of the sensor. The zero-point correction is conducted in a state where no acceleration of the vehicle is occurring. In this zero-acceleration state, the peripheral acceleration of the wheel $a_{wf}$ is also expected to be zero. Actually, the peripheral acceleration of the wheel $a_{wf}$ does not rest at zero because of irregularity of the road surface or slippage of the wheel. Therefore, if the peripheral acceleration of the wheel $a_{wf}$ falls x times in a predetermined range of a small value, it is decided that the acceleration of the vehicle $G_x$ is substantially zero. In this condition, if there is any value outputted from the body accelerometer 22, a correction signal is outputted from the zero-point correcting circuit 42, and thus a zero-point corrected acceleration of the vehicle $G_x$ is obtained. The zero-point corrected $G_{x'}$ together with the peripheral acceleration of the wheel $a_{wf}$, is outputted to the vehicle velocity estimating circuit 44a (Step S2).

Then, in the vehicle velocity estimating circuit 44a, a decision is made as to whether the absolute value of the acceleration of the vehicle $G_x$ is greater than a predetermined value $\beta (|G_x|>\beta$, where $\beta > 0)$ (Step S3). If $|G_x|<\beta$, it is decided that there is no acceleration. If $|G_x|>\beta$, it is decided that there is no acceleration. The threshold value $\beta$ has been introduced in order to obtain a stable decision on the acceleration of the vehicle $G_x$ in the presence of noise.

If it is decided in Step S3 that there is no acceleration $(|G_x|<\beta)$, it is then decided whether the wheel velocity $V_{wf(n)}$ inputted this time is greater than an estimated velocity of the vehicle $V_{reff(n-1)}$ obtained in the previous computation (Step S4). If the answer is YES in Step S4, then the estimated velocity of the vehicle $V_{reff(n)}$ is determined by the following equation (Step S5):

$$V_{reff(n)} = V_{reff(n-1)} + G_1 \times t$$

where $G_1 (>0)$ is a preset acceleration and t is a computing interval.

If the answer is NO in Step S4, it is then decided whether the estimated velocity of the vehicle $V_{reff(n-1)}$ is greater than the wheel velocity $V_{wf(n)}$ (Step S6). If the answer is YES in Step S6, then the estimated velocity of the vehicle $V_{reff(n)}$ is determined as follows (Step S7):

$$V_{reff(n)} = V_{reff(n-1)} - G_2 \times t$$

where $G_2 (>0)$ is a preset deceleration and t is a computing interval.

If the answer is NO in Step S6, that is, the estimated velocity of the vehicle $V_{reff(n-1)}$ is not greater than the wheel velocity $V_{wf(n)}$, then the estimated velocity of the vehicle $V_{reff(n)}$ is determined as follows (Step S8):

$$V_{reff(n)} = V_{reff(n-1)}$$

As has been described in Steps S4 through S8, the wheel velocity $V_{wf(n)}$ is compared with the estimated velocity of the vehicle $V_{reff(n-1)}$. Then, the estimated velocity of the vehicle $V_{reff(n)}$ is calculated based on the result of comparison. As a result, the estimated velocity of the vehicle $V_{reff(n)}$ can be determined with high accuracy as shown in FIGS. 4 and 5.

On the other hand, when the wheels of the motorcycle 10 slip on the road surface upon deceleration, for example, the difference between the peripheral velocity of the wheel $V_{wf}$ and the actual velocity of the vehicle $V_i$ increases, as shown in FIG. 4. Thus, when the estimated velocity of the vehicle $V_{reff(n)}$ is calculated based on the peripheral velocity of the wheel $V_{wf(n)}$ as described in Steps S4 through S8, an estimated velocity of the vehicle $V_{reff}$ close to the actual velocity of the vehicle $V_i$ cannot be obtained with sufficient accuracy.

When it is decided in step S3 that there is acceleration $(|G_x|>\beta)$, the estimated velocity of the vehicle $V_{reff(n)}$ is determined as follows (Step S9):

$$V_{reff(n)} = V_{reff(n-1)} + \int G_x dt$$

where t represents a computing interval.

Thus, when it is decided that the vehicle is in the accelerated or decelerated state, the estimated velocity of the vehicle $V_{reff(n)}$ can be determined with high accuracy by using the value of the acceleration of the vehicle $G_x$ only.

The estimated velocity of the vehicle $V_{reff}$ is supplied to the slippage ratio calculating circuit 46a together with the peripheral velocity of the wheel $V_{wf}$. The slippage ratio calculating circuit 46a determines a slippage ratio $S_f$ by the following equation using the estimated velocity of the vehicle $V_{reff}$ and the peripheral velocity of the wheel $V_{wf}$.

$$S_f = (V_{reff} - V_{wf})/V_{reff}$$

Figure 6:
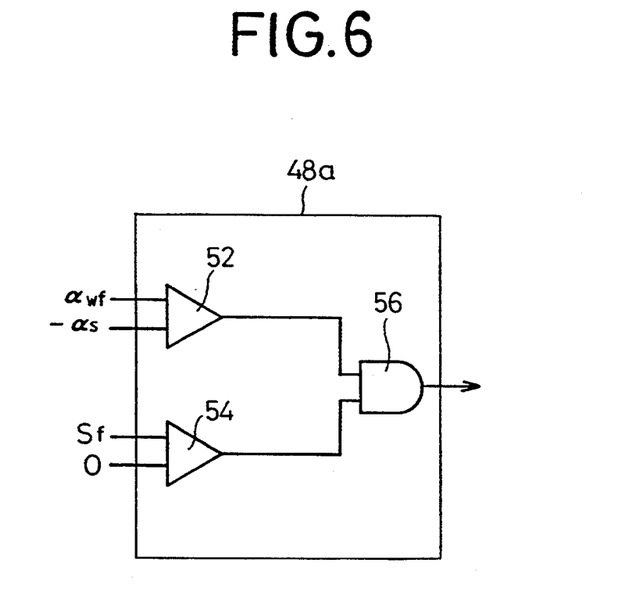
FIG. 6 is a block diagram of a gate signal generating the circuit employed in the device shown in FIG. 1.
Figure 7:
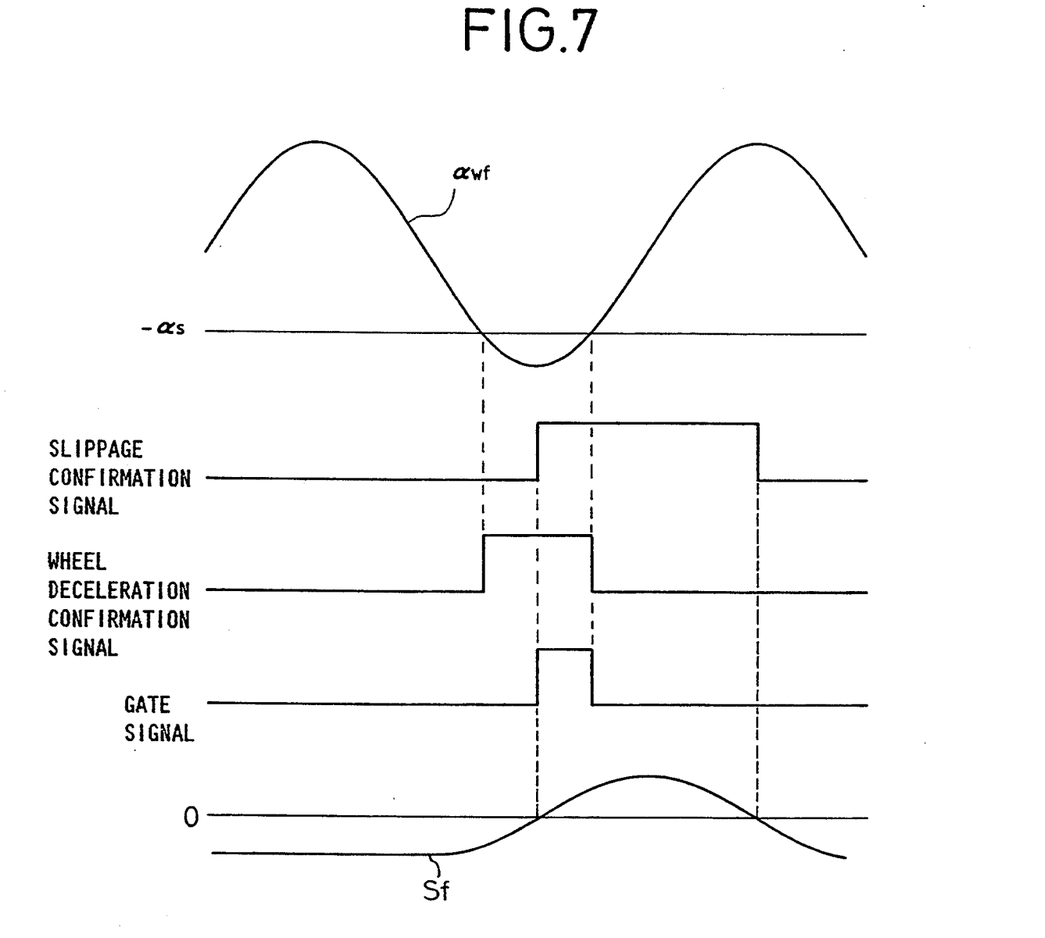
FIG. 7 is a graph for explaining generation of the gate signal in the circuit shown in FIG. 6.

The slippage ratio $S_f$ is outputted to the gate signal generating circuit 48a together with the peripheral acceleration of the wheel $a_{wf}$. As shown in FIG. 6, the gate signal generating circuit 48a comprises a first comparator 52 supplied with the peripheral acceleration of the wheel $a_{wf}$ and a reference value $-a_s$ ($a_s$: positive predetermined value) for decision, a second comparator 54 supplied with a slippage ratio $S_f$ and a reference value 0, and an AND circuit 56 supplied with the outputs of the comparators 52 and 54. In the gate signal generating circuit 48a, the second comparator 54 generates a slippage confirmation signal which goes to a high level when $S_f > 0$, that is, when each wheel is slipping on the road surface, as shown in FIG. 7. The first comparator 52 produces a wheel deceleration confirmation signal which goes to a high level when $a_{wf} \leq -a_s$ ($a_s$: positive predetermined value), that is, the peripheral acceleration of the wheel $a_{wf}$ is equal to or less than a predetermined deceleration. The AND circuit 56 outputs a logical product of both the slippage confirmation signal and the wheel deceleration confirmation signal to the friction coefficient calculating circuit 50, as a gate signal. Incidentally, the generation of the gate signal suggests the possibility that the brake control system will enter into the limiting control mode.

The friction coefficient calculating circuit 50 detects a rise in the gate signal and starts computing the coefficient of friction. The slippage ratio $S_r$ of the rear wheel 16, which has been determined in the same manner as that of the front wheel 14, and the acceleration of the vehicle $G_x$ are supplied to the friction coefficient calculating circuit 50.

In the friction coefficient calculating circuit 50, the coefficient of friction $\mu_f$ between the road surface and the front wheel 14 is determined from the following equation based on the slippage ratio $S_r$ of the rear wheel 16 and the acceleration of the vehicle $G_x$:

$$\mu_f = (A - B \cdot K_x) \cdot G_x,$$

where A and B are constants, and $K_x$ represents a coefficient set in advance according to the slippage ratio $S_r$ of the rear wheel 16 in order to determine the coefficient of friction $\mu_f$ between the road surface and the front wheel 14 regardless of the braking force of the rear wheel 16.

That is, when the coefficient of friction $\mu_f$ between the road surface and the front wheel 14 is determined from the acceleration of the vehicle $G_x$, the term $B \cdot K_x \cdot G_x$ as a correction term related to the slippage ratio $S_r$ of the rear wheel 16 is subtracted from the term $A \cdot G_x$. Thus, an accurate value of the coefficient of friction $\mu_f$ between the road surface and the front wheel 14 can be obtained.

Similarly to the front wheel 14, a gate signal is produced only when both the peripheral acceleration $\alpha_{wr}$ and the slippage ratio $S_r$ of the rear wheel 16 respectively satisfy predetermined conditions. In this condition, the coefficient of friction $\mu_r$ between the road surface and the rear wheel 16 can be determined based on the slippage ratio $S_f$ of the front wheel 14 and the acceleration of the vehicle $G_x$. (See the dashed line in FIG. 1).

As described above, the device 30 makes the friction coefficient calculating circuit 50 start to calculate the coefficients of friction $\mu_f$ and $\mu_r$ during the normal control mode of the brake control system, in response to the gate signals supplied from the gate signal generating circuits 48a and 48b. Thus, as the coefficients of friction $\mu_f$ and $\mu_r$ have already been calculated when the normal control mode is shifted into the limiting control mode, a suitable target slippage ratio can be set. As a result, the braking can be controlled properly.

When the coefficients of friction $\mu_f$ and $\mu_r$ are determined from the acceleration of the vehicle $G_x$, a braking force of the opposite wheel is not included in the values of the coefficients of friction $\mu_f$ and $\mu_r$ due to the correction term of $B \cdot K_x \cdot G_x$. Thus, the coefficients of friction $\mu_f$ and $\mu_r$ can be determined with higher accuracy.

The coefficients of friction $\mu_f$ and $\mu_r$ can be similarly determined in the case of acceleration, by causing the gate signal generating circuit 48a to produce a wheel acceleration confirmation signal under the condition of $\alpha_{wf} \geq -\alpha_s$ ($\alpha_s$: positive predetermined value).

The device for calculating the coefficients of friction according to the present invention can bring about the following advantageous effects.

The calculation instructing signal is outputted from a calculation instructing means only when the slippage ratio and the peripheral acceleration of one of the front and rear wheels respectively satisfy predetermined conditions. Then, the friction coefficient calculating means calculates the coefficient of friction between the road surface and one wheel based on the acceleration of the vehicle and the slippage ratio of the other wheel in response to the above signal. Thus, if the predetermined conditions are suitably set up, then the coefficients of friction can be obtained prior to entering the antilock control mode. Therefore, a suitable target slippage ratio can be established beforehand, and a stable control of the braking of the vehicle can be attained. In the case where the slippage ratio of one of the wheels is positive and the deceleration of the wheel reaches a predetermined value or larger, the vehicle is being braked and slipping. In such a state, a further increase in slippage ratio tends to occur. Thus, if the coefficients of friction are determined in this state, then the optimum target slippage ratio can be prepared prior to entering the antilock control mode.

Having now fully described the invention, it will be apparent to those skilled in the art that many changes and modification can be made without departing from the spirit or scope of the invention as set forth herein.

What is claimed is:

1. An antilock braking control device for calculating the coefficient of friction between a wheel and a road surface, for use in a vehicle having front and rear wheels, and applying a controlled braking force to the vehicle, comprising:

a pair of sensors disposed respectively proximate said front and rear wheels of said vehicle for detecting a rate of rotation of said respective wheels;

means for calculating respective peripheral velocities of said front and rear wheels based on outputs from said sensors;

first slippage ratio calculating means for calculating a slippage ratio of one of said front and rear wheels based on a peripheral velocity of said one wheel and the velocity of the vehicle;

second slippage ratio calculating means for calculating a slippage ratio of the other wheel from a peripheral velocity of said other wheel and the velocity of the vehicle;

vehicle acceleration detecting means disposed on said vehicle for detecting acceleration or deceleration of the vehicle;

wheel acceleration calculating means for calculating peripheral acceleration or deceleration of said one wheel based on the peripheral velocity of said one wheel;

instructing means for generating a calculation starting signal when the slippage ratio of said one wheel and the peripheral acceleration of said one wheel respectively satisfy predetermined conditions;

friction coefficient calculating means for calculating the coefficient of friction between the road surface and said one wheel based on the slippage ratio of said other wheel and said acceleration or deceleration of the vehicle detected in response to said calculating starting signal, wherein said coefficient of friction is calculated prior to initiating an antilock control mode in response to said calculation starting signal; and means for applying a braking force to said one wheel, wherein said braking force is increased until a target slip ratio is reached, and thereafter said braking force is controlled in said antilock control mode in order to maintain said target slip ratio, said target slip ratio being set based on said coefficient of friction detected prior to initiating said antilock control mode.

2. A device according to claim 1, wherein said instructing means generates a calculation starting signal when the peripheral acceleration of said one wheel reaches or exceeds a predetermined value and the slippage ratio of said one wheel becomes positive.

3. A device according to claim 1 or 2, wherein said friction coefficient calculating means determines the coefficient of friction between the road surface and said one wheel, by an equation:

$$\mu = (A - B \cdot K_x) \cdot G_x,$$

where $\mu$ represents the friction coefficient of a road surface on one wheel side; A and B are constants; $K_x$ is a constant set according to the slippage ratio of the other wheel in order to determine the coefficient of friction $\mu$ between the road surface and the one wheel regardless of the braking force of the other wheel; and $G_x$ represents acceleration of the vehicle.

* * * * *